United States Patent [19]

Mueller-Tamm et al.

[11] 4,229,318
[45] Oct. 21, 1980

[54] MANUFACTURE OF A TITANIUM-CONTAINING COMPONENT FOR CATALYSTS OF THE ZIEGLER-NATTA TYPE

[75] Inventors: Heinz Mueller-Tamm; James F. R. Jaggard, both of Ludwigshafen; Hans Schick, Mannheim, all of Fed. Rep. of Germany

[73] Assignee: BASF Aktiengesellschaft, Fed. Rep. of Germany

[21] Appl. No.: 935,948

[22] Filed: Aug. 23, 1978

[30] Foreign Application Priority Data

Sep. 1, 1977 [DE] Fed. Rep. of Germany ....... 2739382

[51] Int. Cl.$^3$ .............................................. B01J 31/02
[52] U.S. Cl. .................................................. 252/429 B
[58] Field of Search .................................... 252/429 B

[56] References Cited

U.S. PATENT DOCUMENTS

| | | | |
|---|---|---|---|
| 3,701,763 | 10/1972 | Wada et al. | 252/429 B |
| 3,992,320 | 11/1976 | Schneider et al. | 252/429 B |
| 4,120,823 | 10/1978 | Tamm et al. | 252/429 B |
| 4,135,045 | 1/1979 | Matsuzawa et al. | 252/429 B |
| 4,145,312 | 3/1979 | Matheson | 252/429 B |

*Primary Examiner*—Helen M. S. Sneed
*Attorney, Agent, or Firm*—Keil & Witherspoon

[57] ABSTRACT

A process for the manufacture of a titanium-containing component of a catalyst for the Ziegler-Natta polymerization of α-monoolefins, by (a) milling a titanium-containing compound of the general formula $TiCl_3 \cdot nAlCl_3$ (where n is a number from 0.01 to 1) with (b) an ether of a particular type or an ester of a particular type, wherein (1) a vibratory ball mill giving a relatively high milling acceleration is used, (2) the mill is first charged with the titanium-containing compound (a), after which it may or may not be run for a certain period, thereafter (3) while milling, the amount of the ether or ester (b) which corresponds to a particular molar ratio of aluminum in the titanium-containing compound (a) to ether or ester (b) is added continuously or in small portions, then (4) the batch is milled for a certain period, after which (5) the product obtained from stage (4) may or may not be washed with a hydrocarbon and dried, and following which (6) the product obtained from stage (4) or (5) may or may not be milled for a certain period at a low temperature, next (7) the product obtained from stage (4), (5) or (6) is brought together with a liquid silicon compound of a particular type or a liquid tin compound of a particular type (these compounds acting as promoters) and the batch is left for a certain period and is then separated into a solid-phase product and into a liquid-phase product, and thereafter (8) the solid-phase product obtained from stage (7) is washed with a hydrocarbon or with one of the promoters mentioned under (7) and is dried, following which (9) the product obtained from stage (8) may or may not be milled for a certain period at a low temperature.

Using the titanium-containing catalyst components thus obtainable makes it possible to produce polymers, having a high stereoregularity, in high specific yields.

7 Claims, No Drawings

MANUFACTURE OF A TITANIUM-CONTAINING COMPONENT FOR CATALYSTS OF THE ZIEGLER-NATTA TYPE

The present invention relates to a process for the manufacture of a titanium-containing component of a catalyst for the Ziegler-Natta homopolymerization or copolymerization of α-monoolefins of 3 to 6 carbon atoms by milling together.

(a) a titanium-containing compound of the general formula $$TiCl_3 \cdot nAlCl_3$$

where n is a number from 0.01 to 1 and (b) an ether of a total of 4 to 30 carbon atoms, having the general formula $$R^1—O—R^2$$

where

R$^1$ and R$^2$ may be identical or different and represent (I) open-chain alkyl of 2 to 15 carbon atoms, (II) phenyl or (III) alkylphenyl, where alkyl is of 1 to 8 carbon atoms, or an ester of a total of 2 to 34 carbon atoms, having the general formula $$R^3—O—CO—R^4$$

or $$R^3—O—CO—C=CH$$
$$\phantom{R^3—O—CO—}|\phantom{C}|$$
$$\phantom{R^3—O—CO—}R^4\phantom{C}R^4$$

where

R$^3$ is (I) alkyl of 1 to 16 carbon atoms or (II) phenylalkyl of a total of 7 to 23 carbon atoms, in which up to 5 hydrogens of the phenyl may be substituted by alkyl of 1 to 4 carbon atoms, and R$^4$ is (I) hydrogen, (II) alkyl of 1 to 18 carbon atoms, (III) phenylalkyl of a total of 7 to 23 carbon atoms, in which up to 5 hydrogens of the phenyl may be substituted by alkyl of 1 to 4 carbon atoms, (IV) phenyl or (V) alkylphenyl of a total of 7 to 23 carbon atoms, in which up to 4 hydrogens of the phenyl may be substituted by alkyl of 1 to 5 carbon atoms.

A plurality of embodiments of processes of this type is known. The object of such processes is primarily to obtain a titanium-containing component which, after activation with an organo-aluminum compound or the like, gives a catalyst which in the polymerization of α-monoolefins produces a high specific yield of poly-α-olefins and/or produces a poly-α-olefin having a relatively high proportion of stereoregular polymer.

The conventional processes have had substantial success; however, it is a certain disadvantage that the relevant titanium-containing components, when used in Ziegler-Natta catalysts for the polymerization of α-olefins, either give polymers which have a relatively high stereoregularity (isotacticity) but in relatively low specific yield, or give a relatively high specific yield of polymers of relatively low stereoregularity.

It is an object of the present invention to provide a process of the initially defined type, by means of which it is possible to obtain a titanium-containing component which exhibits the above disadvantage to a substantially lesser degree, if at all.

We have found that this object is achieved if certain specific physical milling conditions are used and the starting materials are brought together in a particular manner and milled with one another for a certain period, following which the product may or may not be subjected to a particular intermediate treatment, the product is then treated with a selected promoter and thereafter the resulting solid-phase product is isolated, following which it may or may not be milled further, at a low temperature.

Accordingly, the present invention relates to a process for the manufacture of a titanium-containing component of a catalyst for the Ziegler-Natta homopolymerization or copolymerization of α-monoolefins of 3 to 6 carbon atoms, by milling together (a) a titanium-containing compound of the general formula $$TiCl_3 \cdot nAlCl_3$$

where n is a number from 0.01 to 1, especially from 0.1 to 0.4, and (b) an ether of a total of 4 to 30, especially of 6 to 16, carbon atoms, having the general formula $$R^1—O—R^2$$

where

R$^1$ and R$^2$ may be identical or different and represent (I) open-chain alkyl of 2 to 15, especially of 3 to 18, carbon atoms, (II) phenyl or (III) alkylphenyl, where alkyl is of 1 to 8 carbon atoms, or an ester of a total of 2 to 34, especially of 2 to 18, carbon atoms, having the general formula $$R^3—O—CO—R^4$$

or $$R^3—O—CO—C=CH$$
$$\phantom{R^3—O—CO—}|\phantom{C}|$$
$$\phantom{R^3—O—CO—}R^4\phantom{C}R^4$$

where

R$^3$ is (I) alkyl of 1 to 16, especially of 1 to 8, carbon atoms or (II) phenylalkyl of a total of 7 to 23, especially of 7 to 14, carbon atoms, in which up to 5 hydrogens of the phenyl may be substituted by alkyl of 1 to 4 carbon atoms, and R$^4$ is (I) hydrogen, (II) alkyl of 1 to 18, especially of 2 to 12, carbon atoms, (III) phenylalkyl of a total of 7 to 23, especially of 7 to 14, carbon atoms in which up to 5 hydrogens of the phenyl may be substituted by alkyl of 1 to 4 carbon atoms, (IV) phenyl or (V) alkylphenyl of a total of 7 to 23, especially of 7 to 14, carbon atoms, in which up to 4 hydrogens of the phenyl may be substituted by alkyl of 1 to 5 carbon atoms, wherein (1) a vibratory ball mill having a milling acceleration of from 30 to 80, especially from 45 to 55, m.sec$^{-2}$ is used, (2) the mill is first charged with the titanium-containing compound (a), after which it may or may not be run at from −50° to +100° C., especially from −30° to +50° C., for a period of from 0.5 to 100, especially from 2 to 20, hours in the absence of a diluent, thereafter (3) whilst milling, with the material in the mill at from −50° to +80° C., especially from −30° to +60° C., the amount of the ether or ester (b) which corresponds to a molar ratio of aluminum in the titanium-containing compound (a) to ether or ester (b) of from 1:5 to 1:0.05, especially from 1:2 to 1:0.7, is added continuously or in small portions, at a rate of from 0.01 to 200, especially from 1 to 80, ml per minute per 2.5 kg of titanium-containing compound (a), in the absence of a diluent, then (4) the material in the mill is brought to from +10° to +100° C., especially from +20° to +60° C., whilst being milled, and is kept in this temperature range for from 5 to 150, especially from 15 to 80, hours, after which (5) the product obtained from stage (4) may or may not be washed with at least 0.6 times its amount by weight of a hydrocarbon which is liquid under normal conditions and boils below 150° C., especially below 100° C., and is dried, and following which (6) the product obtained from stage (4) or (5) may or may not be milled for a period of from 5 to 60, especially from 10 to 30, minutes at from −50° to −10° C., especially from −30° to −10° C., in the absence of a diluent, next (7) the product obtained from stage (4), (5) or (6) is brought together with at least 0.5 times its amount by weight of a promoter of the general formula $SiX_xR^5_{4-x}$ with the proviso that if two or more radicals $R^5$ are present in the compound, these radicals are identical with one another, or of the general formula $SiX_yR^5_{4-y}$ with the proviso that if two or more radicals $R^5$ are present in the compound, at least two of these radicals are different from one another, or of the general formula $SnX_yR^5_{4-y}$, $Si(OR^5)_zR^5_{4-z}$ or $SiPhR^5_3$ with the proviso that if two or more radicals $R^5$ are present in the compound, these radicals are identical with one another or at least two of these radicals are different from one another,
in which general formulae
x is from 0 to 4, especially from 1 to 3,
y is from 0 to 3, especially from 1 to 3,
z is from 1 to 3,
X is halogen, especially chlorine,
$R^5$ is (I) hydrogen, with the proviso that in none of the compounds more than three of these radicals are hydrogen, (II) alkyl of 1 to 12, especially of 1 to 6, carbon atoms or (III) phenyl, and
Ph is phenyl, in which from 0 to 5 hydrogens of the phenyl may be substituted by alkyl or alkoxy of 1 to 5 carbon atoms, phenyl or phenoxy, chlorine or trialkylsilyl, where alkyl is of 1 to 5 carbon atoms, and the batch is kept at from 0° to 250° C., especially from 20° to 150° C., for a period of from 0.2 to 10, especially from 0.5 to 5, hours and is separated into a solid-phase product and a liquid-phase product, and thereafter (8) the solid-phase product obtained from stage (7) is washed with at least 0.4 times its amount by weight of a hydrocarbon which is liquid under normal conditions and boils below 150° C., especially below 100° C., or of a promoter listed under (7), and is dried, following which (9) the product obtained from stage (8) may or may not be milled for a period of from 5 to 60, especially from 10 to 30, minutes at from −50° to 0° C., especially from −30° to −10° C., in the absence of a diluent.

With regard to the materials used in the novel process, the following may be noted:

The titanium-containing compounds (a) having the stated general formula are the relevant conventional compounds, eg. those obtained by co-crystallizing $TiCl_3$ and $AlCl_3$ or by reducing $TiCl_4$ by means of aluminum or of mixtures of aluminum and titanium. Co-crystallized compounds of the formula $TiCl_3.(\frac{1}{3})AlCl_3$ are particularly suitable. Appropriate titanium-containing compounds (a) are commercially available and further discussion is therefore unnecessary.

Suitable ethers (b) having the stated general formula are again the relevant conventional ethers of this formula, especially those where $R^1$ and/or $R^2$ is methyl, ethyl, propyl, butyl, amyl, hexyl or phenyl. Suitable compounds of this type are described, for example, in U.S. Pat. No. 3,116,274.

Specific examples of very suitable ethers (b) are di-n-propyl, di-n-butyl, di-n-amyl, di-isoamyl and di-n-hexyl ether, methyl phenyl ether and ethyl phenyl ether.

Amongst the above, di-n-butyl ether, di-isoamyl ether and methyl phenyl ether are more particularly suitable.

Suitable esters (b), having the stated general formula, are again the relevant conventional esters of this formula, especially those where $R^3$ is methyl, ethyl, propyl, n-butyl, n-pentyl, i-pentyl, n-hexyl or benzyl, and $R^4$ is hydrogen or methyl, ethyl, n-propyl, n-butyl, n-pentyl, i-pentyl, n-hexyl, n-heptyl, n-octyl, phenyl, benzyl, 1-phenylethyl, 2-phenylethyl, 3-phenylpropyl, 4-phenylbutyl or 5-phenylpentyl.

Specific examples of very suitable esters (b) are ethyl acetate, butyl acetate, ethyl propionate, ethyl n-butyrate, ethyl n-valerate, ethyl phenylacetate, ethyl 3-propionate, ethyl 4-phenylbutyrate, butyl acrylate and butyl methacrylate.

Ethyl propionate, ethyl n-valerate, ethyl phenylacetate, ethyl 3-phenylpropionate, ethyl 4-phenylbutyrate and butyl methacrylate are more particularly suitable.

Suitable promoters are especially those where, in the above general formula, $R^5$ is methyl, ethyl, n-propyl, i-propyl, n-butyl, i-butyl, n-pentyl, i-pentyl or n-hexyl, and Ph is phenyl, monoalkoxyphenyl, dialkoxyphenyl, monochlorophenyl, dichlorophenyl, monoalkylphenyl, dialkylphenyl, mono-(trimethylsilyl)-phenyl or di-(trimethylsilyl)-phenyl.

Specific examples of very suitable promoters are methyltrichlorosilane, dimethyldichlorosilane, trimethylchlorosilane, dimethylphenylchlorosilane, phenyltrichlorosilane, diphenyldichlorosilane, tetramethylsilane, triethylsilane, phenyltrimethylsilane, o-, m- and p-methylphenyltrimethylsilane, triethylchlorostannane and tri-n-butylchlorostannane.

Trimethylchlorosilane, phenyltrimethylsilane, m-methylphenyltrimethylsilane and tri-n-butylchlorostannane and more especially suitable.

The liquid hydrocarbon used in stages (5) and (8) may be a hydrocarbon of the type which is conventionally brought together with a titanium-containing component for a Ziegler-Natta catalyst, for example in the polymerization of α-monoolefins, without damaging the catalyst or its titanium-containing component. Examples of suitable hydrocarbons are pentanes, hexanes, heptanes, gasolines and cyclohexane.

The process according to the invention is simple to carry out and is, without further explanations, within the abilities of those skilled in the art. It is merely necessary to note the following in respect to the optional measures, ie. the operation or non-operation of the mill in stage (2), and the implementation or non-implementation of stages (5), (6) and (9):

Milling in stage (2) is, in general, indicated if the titanium-containing compound (a) employed is of relatively coarse particle size.

Implementation of stage (5) is generally advisable if the product obtained from stage (4) is tacky.

We have found that implementation of stage (6) is advantageous if the product obtained from stage (4) or (5) is still of relatively coarse particle size.

The implementation of stage (9) is in general advantageous if the resulting catalyst component is to be employed as such, ie. in a dry, easily metered condition.

The titanium-containing components, manufactured by the process of the invention, for catalysts of the Ziegler-Natta type, can be employed, in the polymerization of α-olefins, in the relevant conventional manner, ie. in general by using them together with an organometallic activator, especially with an aluminum-alkyl of the general formula Al(alkyl)$_3$ or ClAl(alkyl)$_2$, where alkyl is of 1 to 8 carbon atoms, and above all with triethyl-aluminum or diethyl-aluminum chloride.

Particularly good results are obtained in the dry polymerization of α-olefins, ie. in polymerization in the absence of auxiliary liquid media; however, polymerization in the presence of such media can also be carried out very successfully. The molecular weight can be adjusted by using the conventional regulators, especially hydrogen. Suitable α-olefins to use in the polymerization are those of 3 to 6 carbon atoms, especially propylene, 1-butene and 4-methyl-1-pentene.

EXAMPLE 1

Manufacture of the titanium-containing component

The starting materials are
(a) a titanium compound of the formula TiCl$_3$.$\frac{1}{3}$AlCl$_3$ and
(b) diethyl ether.

Milling is carried out in a vibratory ball mill having a useful volume of 10 liters.

Further details are as follows:
(1) the mill is operated with a milling acceleration of 47 m.sec$^{-2}$,
(2) the mill is first charged with 2.2 kg of the titanium-containing compound (a) and is operated at +35° C. for a period of 16 hours in the absence of a diluent, then
(3) whilst milling, with the material in the mill at −12° C., the amount of the ether (b) corresponding to a molar ratio of aluminum in the titanium-containing compound (a) to ether (b) of 1:1 is added continuously at a rate of 9.5 ml/minute per 2.5 kg of titanium-containing compound (a), in the absence of a diluent, after which
(4) the material in the mill is brought to +36° C., whilst milling, and is kept at this temperature for 17 hours, following which
(5) the product obtained from stage (4) is washed with 0.75 times its amount by weight of hexane and is dried, next
(6) the product obtained from stage (5) is milled for a period of 25 minutes at −15° C. in the absence of a diluent, thereafter
(7) the product obtained from stage (6) is brought together with 1.2 times its amount by weight of trimethylchlorosilane, and the batch is kept at +58° C. for a period of 1 hour and is separated into a solid-phase product and a liquid-phase product, and then
(8) the solid-phase product obtained from stage (7) is washed with 4.1 times its amount by weight of heptane and is dried.
(9) Stage 9 is omitted.

Polymerization by means of the titanium-containing component 1.0 g of the titanium-containing component and 1.8 g of diethyl-aluminum chloride are introduced into a 2 liter stirred flask containing 1.5 l of dry heptane. Polymerization is then carried out whilst stirring, at a propylene pressure of 1 bar and at 60° C. (both these parameters being regulated to constant values) for a period of 5 hours, after which the polymerization is stopped by adding 20 ml of methanol. The suspension medium is then removed by distillation.

This gives 101 g of polypropylene, corresponding to a productivity of 122 parts by weight of polypropylene per part by weight of titanium-containing compound (a), calculated as TiCl$_3$. The polypropylene contains 1.75% by weight of material soluble in boiling n-heptane.

EXAMPLE 2

Manufacture of the titanium-containing component

The starting materials are
(a) a titanium compound of the formula TiCl$_3$.$\frac{1}{3}$AlCl$_3$ and
(b) ethyl valerate.

Milling is carried out in a vibratory ball mill having a useful volume of 10 liters.

Further details are as follows:
(1) the mill is operated with a milling acceleration of 47 m.sec$^{-2}$,
(2) the mill is first charged with 2.4 kg of the titanium-containing compound (a) and is operated at +36° C. for a period of 16 hours in the absence of a diluent, then
(3) whilst milling, with the material in the mill at −15° C., the amount of the ester (b) corresponding to a molar ratio of aluminum in the titanium-containing compound (a) to ester (b) of 1:1 is added continuously at a rate of 10 ml/minute per 2.5 kg of titanium-containing compound (a), in the absence of a diluent, after which
(4) the material in the mill is brought to +40° C., whilst milling, and is kept at this temperature for 26 hours, following which (5) stage 5 is omitted,
(6) the product obtained from stage (4) is milled for a period of 15 minutes at −20° C. in the absence of a diluent, thereafter
(7) the product obtained from stage (6) is brought together with 1.3 times its amount by weight of trimethylchlorosilane, and the batch is kept at +58° C. for a period of 1.5 hours and is separated into a solid-phase product and a liquid-phase product, and then
(8) the solid-phase product obtained from stage (7) is washed with 3.8 times its amount by weight of heptane and is dried, and finally
(9) the product obtained from stage (8) is again milled for a period of 12 minutes, at −18° C., in the absence of a diluent.

Polymerization by means of the titanium-containing component 1.0 g of the titanium-containing component and 1.8 g of diethyl-aluminum chloride are introduced into a 2 liter stirred flask containing 1.5 l of dry heptane. Polymerization is then carried out whilst stirring, at a propylene pressure of 1 bar and at 60° C. (both these parameters being regulated to constant values) for a period of 5 hours, after which the polymerization is stopped by adding 20 ml of methanol. The suspension medium is then removed by distillation.

This gives 210 g of polypropylene, corresponding to a productivity of 271 parts by weight of polypropylene per part by weight of titanium-containing compound (a), calculated as $TiCl_3$. The polypropylene contains 1.7% by weight of material soluble in boiling n-heptane.

EXAMPLE 3

Manufacture of the titanium-containing component

The starting materials are
(a) a titanium compound of the formula $TiCl_3 \cdot \frac{1}{3}AlCl_3$ and
(b) ethyl phenylacetate Milling is carried out in a vibratory ball mill having a useful volume of 10 liters.

Further details are as follows:
(1) the mill is operated with a milling acceleration of 47 m.sec$^{-2}$,
(2) the mill is first charged with 2.5 kg of the titanium-containing compound (a) and is operated at +36° C. for a period of 16 hours in the absence of a diluent, then
(3) whilst milling, with the material in the mill at −15° C., the amount of the ester (b) corresponding to a molar ratio of aluminum in the titanium-containing compound (a) to ester (b) of 1:1 is added continuously at a rate of 11 ml/minute per 2.5 kg of titanium-containing compound (a), in the absence of a diluent, after which
(4) the material in the mill is brought to +40° C., whilst milling, and is kept at this temperature for 24 hours, following which
(5) stage 5 is omitted,
(6) the product obtained from stage (4) is milled for a period of 15 minutes at −20° C. in the absence of a diluent, thereafter
(7) the product obtained from stage (6) is brought together with twice its amount by weight of tri-n-butylchlorostannane, and the batch is kept at 60° C. for a period of 1 hour and is separated into a solid-phase product and a liquid-phase product, and then
(8) the solid-phase product obtained from stage (7) is washed with 3.8 times its amount by weight of heptane and is dried.
(9) Stage 9 is omitted.

Polymerization by means of the titanium-containing component 1.0 g of the titanium-containing component and 1.8 g of diethyl-aluminum chloride are introduced into a 2 liter stirred flask containing 1.5 l of dry heptane. Polymerization is then carried out whilst stirring, at a propylene pressure of 1 bar and at 60° C. (both these parameters being regulated to constant values) for a period of 5 hours, after which the polymerization is stopped by adding 20 ml of methanol. The suspension medium is then removed by distillation.

This gives 216 g of polypropylene, corresponding to a productivity of 319 parts by weight of polypropylene per part by weight of titanium-containing compound (a), calculated as $TiCl_3$. The polypropylene contains 1.7% by weight of material soluble in boiling n-heptane.

EXAMPLE 4

Manufacture of the titanium-containing component

The starting materials are
(a) a titanium compound of the formula $TiCl_3 \cdot \frac{1}{3}AlCl_3$ and
(b) ethyl phenylacetate Milling is carried out in a vibratory ball mill having a useful volume of 50 liters.

Further details are as follows:
(1) the mill is operated with a milling acceleration of 48 m.sec$^{-2}$,
(2) the mill is first charged with 20.66 kg of the titanium-containing compound (a) and is operated at +35° C. for a period of 16 hours in the absence of a diluent, then
(3) whilst milling, with the material in the mill at −12° C., the amount of the ester (b) corresponding to a molar ratio of aluminum in the titanium-containing compound (a) to ester (b) of 1:1 is added continuously at a rate of 11 ml/minute per 2.5 kg of titanium-containing compound (a), in the absence of a diluent, after which
(4) the material in the mill is brought to +40° C., whilst milling, and is kept at this temperature for 48 hours, following which
(5) stage 5 is omitted,
(6) the product obtained from stage (4) is milled for a period of 25 minutes at −14° C. in the absence of a diluent, thereafter
(7) the product obtained from stage (6) is brought together with 1.3 times its amount by weight of trimethylchlorosilane, and the batch is kept at 58° C. for a period of 1 hour and is separated into a solid-phase product and a liquid-phase product, and then
(8) the solid-phase product obtained from stage (7) is washed with 3.8 times its amount by weight of heptane and is dried, and finally
(9) the product obtained from stage (8) is again milled for a period of 10 minutes, at −10° C., in the absence of a diluent.

Polymerization by means of the titanium-containing component 1.0 g of the titanium-containing component and 1.8 g of diethyl-aluminum chloride are introduced into a 2 liter stirred flask containing 1.5 l of dry heptane. Polymerization is then carried out whilst stirring, at a propylene pressure of 1 bar and at 60° C. (both these parameters being regulated to constant values) for a period of 5 hours, after which the polymerization is stopped by adding 20 ml of methanol. The suspension medium is then removed by distillation.

This gives 272 g of polypropylene, corresponding to a productivity of 381 parts by weight of polypropylene per part by weight of titanium-containing compound (a), calculated as $TiCl_3$. The polypropylene contains 0.9% by weight of material soluble in boiling n-heptane.

EXAMPLE 5

Manufacture of the titanium-containing component

This is carried out as in Example 4

Polymerization by means of the titanium-containing component

Polymerization is carried out in a stirred reactor of 0.8 m³ capacity under a propylene pressure of 28 bars, regulated to a constant value, and using an amount of hydrogen of 70 liters (S.T.P.)/h, in a bed of 260 kg of fine polypropylene particles, at a reaction temperature of 70° C., which is regulated to a constant value, and in the absence of a solvent or diluent. The reactor is operated continuously, 7.45 g/h of the titanium-containing component and 29 g/h of $(C_2H_5)_2AlCl$ being introduced separately from one another.

The product obtained from the reactor consists of small polypropylene particles (mean particle size about 0.25 mm); it contains 23 ppm (by weight) of titanium and 4.9% by weight of material soluble in boiling n-heptane, and has an intrinsic viscosity of 2.8 [dl/g].

We claim:

1. A process for the manufacture of a titanium-containing component of a catalyst for the Ziegler-Natta homopolymerization or copolymerization of α-monoolefins of 3 to 6 carbon atoms, by milling together (a) a titanium-containing compound of the general formula $$TiCl_3 \cdot nAlCl_3$$

where n is a number from 0.01 to 1 and (b) an ester of a total of 2 to 34 carbon atoms, having the general formula $$R^3-O-CO-R^4$$

or

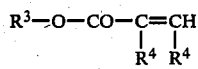

where
R³ is (I) alkyl of 1 to 16 carbon atoms or (II) phenylalkyl of a total of 7 to 23 carbon atoms, in which up to 5 hydrogens of the phenyl may be substituted by alkyl of 1 to 4 carbon atoms, and
R⁴ is (I) hydrogen, (II) alkyl of 1 to 18 carbon atoms, (III) phenylalkyl of a total of 7 to 23 carbon atoms, in which up to 5 hydrogens of the phenyl may be substituted by alkyl of 1 to 4 carbon atoms, (IV) phenyl or (V) alkylphenyl of a total of 7 to 23 carbon atoms, in which up to 4 hydrogens of the phenyl may be substituted by alkyl of 1 to 5 carbon atoms, wherein
(1) a vibratory ball mill having a milling acceleration of from 30 to 80 m.sec⁻² is used,
(2) the mill is first charged with the titanium-containing compound (a), after which it is run at from −50° to +100° C. for a period of from 0.5 to 100 hours in the absence of a diluent, thereafter
(3) whilst milling, with the material in the mill at from −50° to +80° C., the amount of the ester (b) which corresponds to a molar ratio of aluminum in the titanium-containing compound (a) to ester (b) of from 1:5 to 1:0.05 is added continuously or in small portions, at a rate of from 0.01 to 200 ml per minute per 2.5 kg of titanium-containing compound (a), in the absence of a diluent, then (4) the material in the mill is brought to from +10° to +100° C. whilst being milled, and is kept in this temperature range for from 5 to 150 hours, after which
(5) the product obtained from stage (4) is washed with at least 0.6 times its amount by weight of a hydrocarbon which is liquid under normal conditions and boils below 150° C., and is dried, and following which
(6) the product obtained from stage (5) is milled for a period of from 5 to 60 minutes at from −50° to −10° C. in the absence of a diluent, next
(7) the product obtained from stage (6) is brought together with at least 0.5 times its amount by weight of a promoter of the general formula $$SiX_xR^5{}_{4-x}$$

with the proviso that if two or more radicals R⁵ are present in the compound, these radicals are identical with one another, or of the general formula $$SiX_yR^5{}_{4-y}$$

with the proviso that if two or more radicals R⁵ are present in the compound, at least two of these radicals are different from one another, or of the general formula $$SnX_yR^5{}_{4-y},$$

$$Si(OR^5)_zR^5{}_{4-z}$$

or $$SiPhR^5{}_3$$

with the proviso that if two or more radicals R⁵ are present in the compound, these radicals are identical with one another or at least two of these radicals are different from one another,
in which general formulae
x is from 0 to 4,
y is from 0 to 3,
z is from 1 to 3,
X is halogen,
R⁵ is (I) hydrogen, with the proviso that in none of the compounds more than three of these radicals are hydrogen, (II) alkyl of 1 to 12 carbon atoms or (III) phenyl, and Ph is phenyl, in which from 0 to 5 hydrogens of the phenyl may be substituted by alkyl or alkoxy of 1 to 5 carbon atoms, phenyl or phenoxy, chlorine or trialkylsilyl, where alkyl is of 1 to 5 carbon atoms, and the batch is kept at from 0° to 250° C. for a period of from 0.2 to 10 hours and is separated into a solid-phase product and a liquid-phase product, and thereafter (8) the solid-phase product obtained from stage (7) is washed with at least 0.4 times its amount by weight of a hydrocarbon which is liquid under normal conditions and boils below 150° C. or of a promoter listed under (7), and is dried, following which (9) the product obtained from stage (8) is milled for a period of from 5 to 60 minutes at from −50° to 0° C. in the absence of a diluent.

2. A process for the manufacture of a titanium-containing component of a catalyst for the Ziegler-Natta homopolymerization or copolymerization of α-monoolefins of 3 to 6 carbon atoms, by milling together (a) a titanium-containing compound of the general formula $$TiCl_3 \cdot nAlCl_3$$

where n is a number from 0.01 to 1 and (b) an ester of a total of 2 to 34 carbon atoms, having the general formula $$R^3-O-CO-R^4$$

or $$R^3-O-CO-\underset{R^4}{\underset{|}{C}}=\underset{R^4}{\underset{|}{CH}}$$

where $R^3$ is (I) alkyl of 1 to 16 carbon atoms or (II) phenylalkyl of a total of 7 to 23 carbon atoms, in which up to 5 hydrogens of the phenyl may be substituted by alkyl of 1 to 4 carbon atoms, and $R^4$ is (I) hydrogen, (II) alkyl of 1 to 18 carbon atoms, (III) phenylalkyl of a total of 7 to 23 carbon atoms, in which up to 5 hydrogens of the phenyl may be substituted by alkyl of 1 to 4 carbon atoms, (IV) phenyl or (V) alkylphenyl of a total of 7 to 23 carbon atoms, in which up to 4 hydrogens of the phenyl may be substituted by alkyl of 1 to 5 carbon atoms, wherein (1) a vibratory ball mill having a milling acceleration of from 30 to 80 m.sec$^{-2}$ is used, (2) the mill is first charged with the titanium-containing compound (a), after which it is run at from −50° to +100° C. for a period of from 0.5 to 100 hours in the absence of a diluent, thereafter (3) whilst milling, with the material in the mill at from −50° to +80° C., the amount of the ester (b) which corresponds to a molar ratio of aluminum in the titanium-containing compound (a) to ester (b) of from 1:5 to 1:0.05 is added continuously or in small portions, at a rate of from 0.01 to 200 ml per minute per 2.5 kg of titanium-containing compound (a), in the absence of a diluent, then (4) the material in the mill is brought to from +10° to +100° C. whilst being milled, and is kept in this temperature range for from 5 to 150 hours, after which (5) the product obtained from stage (4) is brought together with at least 0.5 times its amount by weight of a promoter of the general formula $$SiX_xR^5_{4-x}$$

with the proviso that if two or more radicals $R^5$ are present in the compound, at least two of these radicals are different from one another, or of the general formula $$SnX_yR^5_{4-y},$$

$$Si(OR^5)_zR^5_{4-z}$$

or $$SiPhR^5_3$$

with the proviso that if two or more radicals $R^5$ are present in the compound, these radicals are identical with one another or at least two of these radicals are different from one another, in which general formulae x is from 0 to 4, y is from 0 to 3, z is from 1 to 3, X is halogen, $R^5$ is (I) hydrogen, with the proviso that in none of the compounds more than three of these radicals are hydrogen, (II) alkyl of 1 to 12 carbon atoms or (III) phenyl, and Ph is phenyl, in which from 0 to 5 hydrogens of the phenyl may be substituted by alkyl or alkoxy of 1 to 5 carbon atoms, phenyl or phenoxy, chlorine or trialkylsilyl, where alkyl is of 1 to 5 carbon atoms, and the bath is kept at from 0° to 250° C. for a period of from 0.2 to 10 hours and is separated into a solid-phase product and a liquid-phase product, and thereafter (6) the solid-phase product obtained from stage (5) is washed with at least 0.4 times its amount by weight of a hydrocarbon which is liquid under normal conditions and boils below 150° C. or of a promoter listed under (5), and is dried.

3. The process set forth in claim 1 or claim 2 wherein said ester (b) is ethyl phenylacetate.

4. The process set forth in claim 1 or claim 2 wherein said promoter is trimethylchlorosilane.

5. The process set forth in claim 2 including prior to stage (5) washing the product obtained from stage (4) with at least 0.6 times its amount by weight of a hydrocarbon which is a liquid under normal conditions and boils below 150° C., and drying the washed product.

6. The process set forth in claim 5 including milling the washed and dried product for a period of from 5 to 60 minutes at from −50° to −10° C. in the absence of a diluent.

7. The process set forth in claim 2 including milling the product obtained from stage (6) for a period of from 5 to 60 minutes at from −50° to 0° C. in the absence of a diluent.

* * * * *

UNITED STATES PATENT AND TRADEMARK OFFICE
CERTIFICATE OF CORRECTION

PATENT NO. : 4,229,318
DATED : October 21, 1980
INVENTOR(S) : HEINZ MUELLER-TAMM, JAMES F.R. JAGGARD and HANS SCHICK It is certified that error appears in the above—identified patent and that said Letters Patent is hereby corrected as shown below:

In claim 2, column 12, line 42: "bath" should read --batch--.

Signed and Sealed this

Tenth Day of March 1981

[SEAL]

Attest:

RENE D. TEGTMEYER

Attesting Officer  Acting Commissioner of Patents and Trademarks